United States Patent
Laermer (10) Patent No.: US 12,240,752 B2
(45) Date of Patent: Mar. 4, 2025

(54) METHOD FOR PRODUCING A SEQUENCING UNIT FOR SEQUENCING A BIOCHEMICAL MATERIAL AND SEQUENCING UNIT

(71) Applicant: Robert Bosch GmbH, Stuttgart (DE)

(72) Inventor: Franz Laermer, Weil Der Stadt (DE)

(73) Assignee: Robert Bosch GmbH, Stuttgart (DE)

( * ) Notice: Subject to any disclaimer, the term of this patent is extended or adjusted under 35 U.S.C. 154(b) by 1015 days.

(21) Appl. No.: 17/051,362

(22) PCT Filed: May 2, 2019

(86) PCT No.: PCT/EP2019/061249
§ 371 (c)(1),
(2) Date: Oct. 28, 2020

(87) PCT Pub. No.: WO2019/215006
PCT Pub. Date: Nov. 14, 2019

(65) Prior Publication Data
US 2021/0229982 A1 Jul. 29, 2021

(30) Foreign Application Priority Data

May 8, 2018 (DE) .................... 10 2018 207 099.7

(51) Int. Cl.
*B81C 1/00* (2006.01)
*B81B 1/00* (2006.01)
*G01N 33/487* (2006.01)

(52) U.S. Cl.
CPC .......... *B81C 1/00087* (2013.01); *B81B 1/004* (2013.01); *G01N 33/48721* (2013.01); *B81B 2201/0214* (2013.01); *B81B 2203/0353* (2013.01); *B81C 2201/0149* (2013.01)

(58) Field of Classification Search
CPC .... B81C 2201/0149; B81C 2201/0156; B81C 2201/0159
See application file for complete search history.

(56) References Cited

U.S. PATENT DOCUMENTS

2013/0240359 A1* 9/2013 Turner ............. G01N 27/44791
204/601
2013/0309776 A1 11/2013 Drndic et al.
2014/0231254 A1* 8/2014 Tung ...................... B81C 3/001
204/601
2015/0206748 A1* 7/2015 Sumant ............... H01L 21/0262
438/481
2016/0187290 A1 6/2016 Leburton

FOREIGN PATENT DOCUMENTS

| CN | 102901763 A | 1/2013 |
| CN | 103789204 A | 5/2014 |
| CN | 106010949 A | 10/2016 |
| WO | 2011/103424 A2 | 8/2011 |

OTHER PUBLICATIONS

International Search Report corresponding to PCT Application No. PCT/EP2019/061249, mailed Jul. 1, 2019 (German and English language document) (5 pages).
Rawlings, C. et al., "High Throuhput Lithography Using Thermal Scanning Probes," 19th International Conference on Solid-State Sensors, Actuators and Microsystems (Transducers), IEEE, Jun. 2017, 418-422 (5 pages).
Schneider, G. F. et al., "DNA Translocation through Graphene Nanopores," Nano Letters, vol. 10, No. 8, Aug. 2010, 3163-3167 (5 pages).
Mashiyama, D. et al., "Nanopatterning of Suspended Graphene Films by Local Catalytic Etching Using Atomic Force Microscopy Equipped with an AG-Coated Probe," Journal of Physical Chemistry C, vol. 119, No. 21, May 2015, 11914-11921 (8 pages).
Merchant et al., "DNA Translocation through Graphene Nanopores", Nano Letters, Jul. 23, 2010, pp. 2915-2921, vol. 10, American Chemical Society (7 pages).

* cited by examiner

*Primary Examiner* — Natalia Levkovich
(74) *Attorney, Agent, or Firm* — Maginot, Moore & Beck LLP (57) ABSTRACT

The disclosure relates to a method for producing a sequencing unit for sequencing a biochemical material. In this case, at least one sequencing pore for sequencing the biochemical material in a precursor layer is created in a thermal lithography process in order to produce a pre-structured layer. The pre-structured layer is then converted into a graphene layer by heating to a conversion temperature in order to produce the sequencing unit. The sequencing pore is reduced to a size suitable for sequencing, depending on the transformation temperature.

16 Claims, 6 Drawing Sheets

METHOD FOR PRODUCING A SEQUENCING UNIT FOR SEQUENCING A BIOCHEMICAL MATERIAL AND SEQUENCING UNIT

This application is a 35 U.S.C. § 371 National Stage Application of PCT/EP2019/061249, filed on May 2, 2019, which claims the benefit of priority to Serial No. DE 10 2018 207 099.7, filed on May 8, 2018 in Germany, the disclosures of which are incorporated herein by reference in their entirety.

BACKGROUND

The disclosure proceeds from a method or a device according to the embodiments.

In the case of so-called self-assembled monolayers of precursor molecules, also called SAMs for short, the precursors dock, for example, with binding sites on a silicon or glass surface, it also being possible for the precursor molecules to crosslink with one another depending on the precursors. These processes are generally self-limiting, i.e., after deposition of a single monolayer and occupation of all available binding spaces of the surface, no further deposition with the same precursor takes place. In most cases, this behavior is achieved by the precursor molecules docking in a selective manner and only on hydrophilic surfaces, generating themselves a hydrophobic surface while doing so, and thus automatically stopping further deposition because further precursor molecules are no longer able to dock on hydrophobic and hence anhydrous surfaces.

Self-assembled monolayers can also be deposited from the liquid phase with the aid of suitable solvents, for example hexane or heptane or else fluorocarbons such as, for instance, FC40. However, owing to the higher purity of the precursor chemistry and to the better quality and reproducibility of the deposited layers, it is vapor deposition that has gained acceptance. This involves converting precursor molecules previously stored as liquid into vapor, for example by heating the precursor liquid. In a reaction chamber, the desired partial pressure of the precursor is set and contacted with the wafer. Methods with or without carrier gas (inert gas or noble gas such as, for example, $N_2$ or Ar) are possible.

Certain SAM coatings can be converted into graphene layers of qualitatively high value on wafers. To this end, the SAM coating after deposition on the substrate surface is, for example, covered with a 300 nm thick metal layer, for instance of nickel or copper, by vapor-coating and subsequently converted into graphene at a high temperature of 800° C. to 1000° C.

SUMMARY

Against this background, the approach presented here presents a method for producing a sequencing unit for sequencing a biochemical material and a sequencing unit as disclosed. Advantageous developments of and improvements to the device specified in the disclosure are possible by the features stated in the embodiments.

The approach presented here is based on the finding that it is possible to predefine nanopores in a graphene layer in a thermal lithography method in a suitable precursor layer, for instance a self-assembled monolayer, and to reduce said nanopores in size to an appropriate diameter upon thermal conversion of the precursor layer into the graphene layer, depending on the conversion temperature. An element produced in this way can, for example, be integrated in a lab-on-a-chip environment which combines quantitative polymerase chain reactions, called qPCR for short, carried out as LATEPCR (linear after the exponential) and the sequencing of DNA fragments according to a Sanger method with determination of DNA fragment length via the nanopores. To produce nanopores in graphene, a thermal lithography method by means of a scanning probe, also called thermal scanning probe lithography or t-SPL for short, can be advantageously used in combination with self-assembled monolayers in order to define and hence create nanopores therein by means of t-SPL even before the conversion of the self-assembled monolayers to graphene, which nanopores leave nanopores suitable for DNA sequencing or determination of DNA fragment length in the generated graphene layer after the thermal conversion of the self-assembled monolayers.

Such nanopores can, for example, be directly burned into graphene by means of an AFM method (AFM=atomic force microscope) by means of electric current pulses. For this purpose, suitable equipment and suitable processes are, however, not available as standard or cannot be obtained commercially, meaning that an adaptation of commercially available AFM tools for this purpose and a corresponding complex process development with respect to the method of burning nanoholes into graphene by means of electric current pulses would be necessary. In contrast, the t-SPL method and corresponding processes for introducing nanostructures into polymers are now commercially and cost-effectively available, specifically both in the form of suitable tools and in the form of suitable processes for nanostructuring polymeric materials. However, graphene is not a polymeric organic material, and so the processes mentioned are not readily transferrable to graphene. However, if nanopores are generated in the organic precursor layer of the graphene in the form of an SAM coating by means of t-SPL, the technology of thermal generation of nanopores is translatable one-to-one into the primary structuring of the SAM coating, i.e., of an organic material. Thereafter, the SAM coating structured in this way can, for example, be thermally converted to graphene under a temporarily applied metal layer, for instance of copper or nickel, the result being that nanopores are generated in the graphene layer in line with the preceding structuring. The resolution limit of the t-SPL method is, for example, 10 to 15 nm, which is too large per se for the intended use, but can, with appropriate control of the thermal conversion of the SAM coating to graphene, ultimately lead to nanopores having diameters of a few nanometers, as are optimal for nanopore sequencing and nanopore determination of DNA fragment length. This means that a commercially available and cost-effective technology is immediately usable for nanostructuring of polymers (the SAM coating material) for subsequently generating defined nanopores in graphene via the structuring of this starting material.

What is presented is a method for producing a sequencing unit for sequencing a biochemical material, the method comprising the following steps:

creating at least one sequencing pore for sequencing the biochemical material in a precursor layer in a thermal lithography method in order to generate a prestructured layer; and converting the prestructured layer into a graphene layer by heating the prestructured layer to a conversion temperature in order to produce the sequencing unit.

In the conversion step, the sequencing pore can be reduced in size to a scale suitable for sequencing the biochemical material, depending on the conversion temperature. In this connection, the suitable scale is, for example, guided by a dimension of the biochemical material. Different diameters of the sequencing pores may be necessary for different biochemical material. Appropriate diameters can be generated by a suitable selection of the conversion temperature. A biochemical material can, for example, be understood to mean a sequence of nucleotides, for instance DNA, or the like. Sequencing can be understood to mean the determination of a sequence of building blocks of the biochemical material, for instance a sequence of nucleotides in a DNA molecule. A sequencing pore can be understood to mean an opening through which the biochemical material can pass during sequencing. A precursor layer can be understood to mean a layer composed of so-called precursor molecules for producing a graphene layer. For example, the precursor layer can be a self-assembled monolayer.

Such precursors can, for example, be organic trichlorosilanes, trimethoxysilanes or triethoxysilanes, for example octyltrichlorosilane, decyltrichlorosilane, octadecyltrichlorosilane, phenyltrichlorosilane, octyltrimethoxysilane, decyltrimethoxysilane, octadecyltrimethoxysilane, phenyltrimethoxysilane, octyltriethoxysilane, decyltriethoxysilane, octadecyltriethoxysilane or phenyltriethoxysilane. Trichlorosilanes are particularly suitable because, owing to their high chemical reactivity, they hydrolyze very rapidly and bond to hydroxyl groups of hydrophilic surfaces and also crosslink rapidly. However, methoxysilanes or ethoxysilanes can also be used. Phenylsilanes, especially trichlorophenylsilane, are particularly suitable for graphene generation because these precursor molecules already contain aromatic carbon rings corresponding to the later graphene structure. In the case of phenyltrichlorosilane, the starting material is in terms of its structure already similar to the target material, and this supports the subsequent thermal conversion of the aromatic carbon rings to graphene.

A thermal lithography method can be understood to mean a thermally controlled nanolithography method, for instance with use of an appropriate scanning probe or tunnel tip having a high tip temperature to burn in the sequencing pore via the high temperature of the tip (t-SPL method). Alternatively, it is also possible to burn a nanopore into a conductive starting material by means of an electric tunnel current pulse.

The method presented here can, for example, be carried out in the context of a total process for producing array cells in silicon with integrated nanopores in graphene. In this case, the sequencing unit can, for example, be combined in a chip comprising a qPCR array.

A diameter of the sequencing pore can be reduced in size to a predetermined diameter in the conversion step. The conversion temperature can be set depending on the predetermined diameter. The predetermined diameter can be selected depending on a characteristic, for example size of the biochemical material to be sequenced. To achieve different predetermined diameters, different conversion temperatures can be used and, for example, selected using a reference table.

According to one embodiment, the sequencing pore can be defined in the form of a nanopoint in the creation step. As a result, the sequencing pore can be created particularly rapidly, for example by means of a temperature-adjusted scanning probe.

The sequencing pore can be created with a diameter of less than 20 nanometers, for example with a diameter between 10 and 20 nanometers, in the creation step. In this case, the range of values from 10 to 20 nanometers arises from the current resolution limit of the t-SPL method, with smaller nanopores being achieved, according to one embodiment, by the subsequent "closing-up method". Accordingly, the sequencing pore can be reduced in size to a diameter between 1 and 5 nanometers, particularly preferably between 1 and 2 nanometers, in the conversion step. This is one way of achieving small pores when it is not possible in an appropriate way to directly produce nanopores of 1 to 5 nanometers or, even better, of 1 to 2 nanometers. Since t-SPL and also most other methods cannot directly achieve this, the mentioned closing-up of the pores is used as an advantageous remedial measure. This "heals" to some extent the insufficient resolution limit of the t-SPL method. This embodiment allows a particularly efficient production of the sequencing unit having the desired pore diameters of 1 to 5 nanometers or, particularly preferably, 1 to 2 nanometers with few production steps.

Moreover, the graphene layer can thereby be formed as a monolayer at least in the edge region of the sequencing pore in the conversion step. As a result, what is made possible is a determination of fragment lengths, for example of DNA fragments, that is as precise as possible when the fragments pass through the sequencing pore.

According to a further embodiment, the sequencing pore can be created in a self-assembled monolayer as the precursor layer in the creation step. A self-assembled monolayer can generally be understood to mean a layer which forms spontaneously on a surface-active or organic substance in the presence of particular reaction conditions and which has a high level of internal order and a defined thickness. As a result, the sequencing pore can be created with high repeatability, high purity and high quality.

Furthermore, the method can comprise a step of applying a metal layer to the prestructured layer. In this case, the prestructured layer can be converted by means of the metal layer in the conversion step. The metal layer can, for example, be a layer of copper or nickel or some other suitable metal or some other suitable metal alloy. The metal layer can serve, inter alia, to heat the prestructured layer. In particular, the metal layer can be a temporary layer which can be removed after the conversion process. As a result, what is made possible is a controlled heating of the prestructured layer and thus a precise size-reduction of the sequencing pore with high repeatability.

It is advantageous when a pore segment of the precursor layer is heated to a temperature above a decomposition temperature of the precursor layer in the creation step in order to create the sequencing pore in the pore segment. A decomposition temperature can be understood to mean a temperature at which the precursor layer decomposes in an oxygenous atmosphere. What is achieved by this embodiment is that the precursor layer in the pore segment is instantly eroded and the sequencing pore is thus practically burnt into the precursor layer extremely rapidly.

According to a further embodiment, the method can comprise a step of generating a cavern element comprising at least one cavern having an entry opening and an exit opening for accommodating the biochemical material. In this case, the precursor layer can be applied before the creation step to a segment of the cavern element that has the exit opening, and the sequencing pore can be created opposite the exit opening in the creation step. A cavern can, for example, be understood to mean a channel-type passage opening in the cavern element. The cavern element can also be generated with multiple caverns. For example, the cavern element can be generated as a cavern wafer. The cavern can, for example, function as a qPCR array cell. An entry opening can be understood to mean an opening through which the cavern can be filled with the biochemical material. In analogy thereto, an exit opening can be understood to mean an opening through which the biochemical material can exit from the cavern. As a result of this embodiment, a cross-section of the exit opening can be controlled and be exactly reduced to a diameter suitable for sequencing the biochemical material.

It is advantageous when, in the generation step, the interior of the cavern is generated with a hydrophilic coating. Additionally or alternatively, a segment of the cavern element that has the surroundings of the entry opening can be generated with a hydrophobic coating. The hydrophilic properties of the cavern interior mean that the filling of the cavern with the biochemical material can be simplified. Moreover, the connection between hydrophilic cavern interior and the hydrophobic surroundings of the cavern entry opening means that an uncontrolled leakage of the biochemical material, i.e., a so-called "carryover", out of the cavern can be avoided.

Thus, the interior of each cavern can have hydrophilic surface properties. By contrast, the surface surroundings of the entry opening can be coated as hydrophobically as possible. These hydrophilic and hydrophobic layers can exercise important roles. According to one embodiment, a hydrophobic layer effect can thus be achieved around the entry openings or between the entry openings of caverns on the surface of the cavern element, i.e., on the wafer surface or chip surface. This can avoid the occurrence of carryover of cavern contents into neighboring caverns via the surface or the formation of electric current paths between neighboring caverns. Therefore, a so-called "crosstalk" can be avoided, i.e., that biomaterial creeps from one cavern into the neighboring cavern via the chip surface and vice versa. Such crosstalk is undesired, and the relatively hydrophobic Si nitride on the chip surface serves to avoid it. The hydrophobic effect of the surface can, according to known prior art, also be enhanced by printing with further hydrophobic layers, for example as a self-assembled monolayer coating (e.g., with PFOTS=perfluorooctyltrichlorosilane, PFD(ecyl)TS, PFO(cta)D(ecyl)TS or the like). According to one embodiment, the interior of the caverns itself is as hydrophilic as possible in order to facilitate filling with aqueous media and to keep the liquid in the cavern interior.

The approach described here further provides a sequencing unit for sequencing a biochemical material. The sequencing unit comprises a graphene layer produced in a method according to any of the preceding embodiments and having at least one sequencing pore for sequencing the biochemical material.

BRIEF DESCRIPTION OF THE DRAWINGS

Exemplary embodiments of the disclosure are depicted in the drawings and more particularly elucidated in the following description, where.

DETAILED DESCRIPTION

In the following description of favorable exemplary embodiments of the present disclosure, identical or similar reference signs are used for the elements which are depicted in the various figures and act in a similar manner, in order to dispense with a repeated description of said elements.

Figure 1:
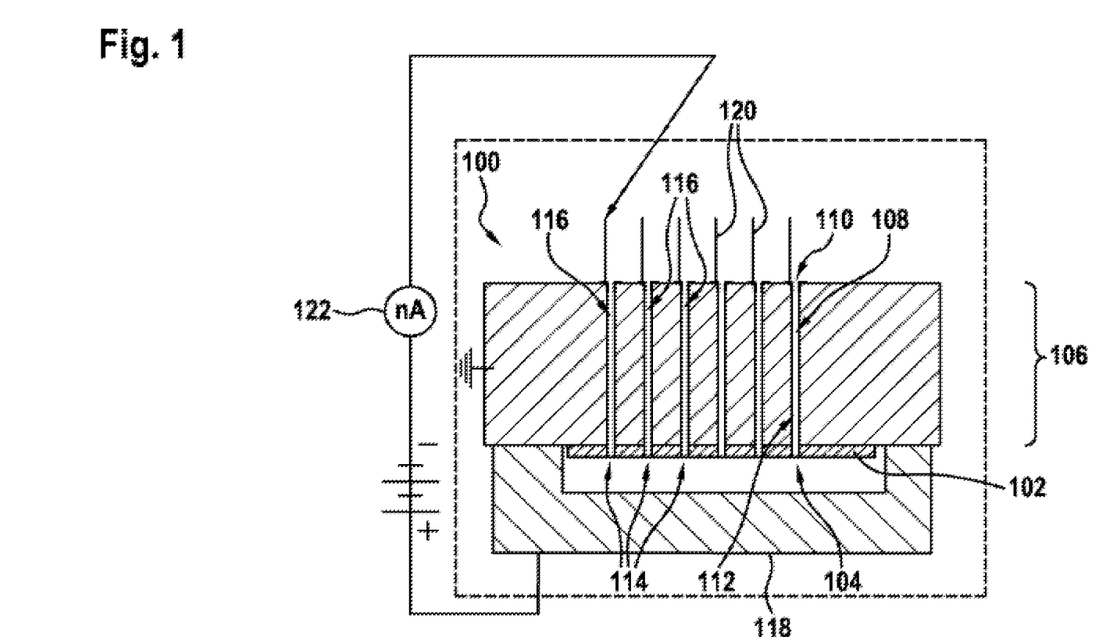
FIG. 1 shows a schematic representation of a sequencing unit according to one exemplary embodiment.

FIG. 1 shows a schematic representation of a sequencing unit 100 according to one exemplary embodiment. The sequencing unit 100 comprises a graphene layer 102 having a sequencing pore 104 for sequencing a biochemical material, in this case for determination of DNA fragment length by way of example. The graphene layer 102 is a layer which was generated by thermal conversion of a self-assembled monolayer prestructured with the sequencing pore 104 in a thermal lithography method. A conversion temperature for the thermal conversion was chosen such that the sequencing pore 104 was reduced in size, as a result of closing up, to a diameter suitable for sequencing the biochemical material. A suitable conversion temperature can therefore be selected depending on the desired diameter of the sequencing pore 104.

According to this exemplary embodiment, the graphene layer 102 forms a base of a cavern element 106 having a cavern 108 for prestorage of the biochemical material. The cavern 108 is, by way of example, formed as a channel crossing the cavern element 106 in a substantially straight manner and having an entry opening 110 and exit opening 112 lying opposite the entry opening. The sequencing pore 104 lies opposite the exit opening 112, meaning that an exit cross-section of the cavern 108 is defined by the sequencing pore 104.

According to the exemplary embodiment shown in FIG. 1, the graphene layer 102 has a plurality of further sequencing pores 114 for sequencing the biochemical material or further biochemical materials. The further sequencing pores 114 are generated analogously to the sequencing pore 104. The cavern element 106 is accordingly formed with multiple further caverns 116 for accommodating the biochemical materials, the respective exit openings of the further caverns 116 each lying opposite one further sequencing pore 114.

The sequencing unit 100 is, for example, integrable in a lab-on-a-chip environment, indicated by a dashed frame. By way of example, the sequencing unit 100 according to FIG. 1 is realized as a bonded component composed of a cavern wafer having nanopores at the base and a cap-shaped counter electrode 118. The graphene layer 102 is covered by the counter electrode 118. The sequencing unit 100 is connected to a measurement device 122 for current measurement via the counter electrode 118 and multiple further electrodes 120 which are each arranged at an entry opening of the caverns 108, 116. In particular, the sequencing unit 100 is realized as a LATE-qPCR Sanger sequencing array in silicon with a downstream graphene-based nanopore sequencer via determination of DNA fragment length.

Self-assembled monolayers, called monolayers for short hereinafter, are absolutely ideal as precursor layer for creating the sequencing pores in the thermal lithography method, especially by thermal scanning probe lithography, t-SPL for short, since precision and reproducibility of this structuring method are particularly good owing to the very low and extremely homogeneous, here monomolecular, layer thickness. Furthermore, at an AFM tip temperature of 900° C. to 950° C., the t-SPL method generates temperatures of 300° C. to 400° C. on the layer surface in a localized and instantaneous manner, this being distinctly above the decomposition temperature of the monolayer in an oxygenous environment, for example in air or in an oxygen-enriched atmosphere or in pure oxygen. The decomposition temperature is, for example, approx. 250° C. As a result, the erosion of the monolayer in the region concerned commences instantly, with the result that the "burning" of a nanopore, also called sequencing pore above, into the monolayer can take place extremely rapidly. Since only comparatively few nanopores are generated across the wafer surface, for example not more than two nanopores per qPCR array cell, and respectively only one or not more than two points are initiated and "burnt" as points per qPCR array cell to this end, the process of producing the sequencing unit 100 is also very economical, since the problems which can occur in connection with dense writing of large surface areas with a multiplicity of differently dimensioned and extended structures are avoided. On the contrary, what is sufficient here per qPCR array cell is the initiation of respectively one or not more than two positions and the "burning" of respectively a single nanopoint or nanodot at each position. Advantageously, points and no complex structural geometries are thus written in the nanometer and micrometer range.

The resolution limit of the t-SPL method is typically between 10 and 15 nm. In the case of nanopores for DNA sequencing via determination of DNA fragment length, this would be somewhat too large and would distinctly reduce the electric signals or the electric signal shift. The mechanism of converting the monolayer into the graphene layer 102 improves the situation significantly because there is usually present in the monolayer for graphene formation an excess of carbon that leads to the formation of graphene bilayers or trilayers, i.e., of multiple layers of graphene instead of a single layer of graphene, also called a monolayer. Owing to the excess of carbon, what occurs in the region of the nanopores is a "closing-up" proceeding from the edges of the nanopores, with the result that the nanopores in the graphene become distinctly smaller than were primarily generated in the monolayer. With optimal process control of the thermal annealing, a nanopore size of 1 to 2 nm can thus be set, the character of the graphene layer 102 changing from a bilayer or trilayer to a monolayer with increasing proximity to a nanopore.

Ideal conditions are thus achieved for the application of nanopore sequencing by means of a preciset possible determination of DNA fragment length via current modulation during passage of fragments through the nanopore: the membrane thickness immediately at the pore opening approximately corresponds to a graphene monolayer with a pore diameter of 1 to 2 nm.

Provided below by way of example is a detailed description of a total process for integrating graphene production with nanopore generation by introduction of self-assembled monolayers and t-SPL into the production of a sequencing qPCR array. The specified dimensions and layer thicknesses or layer materials used in the process flow are merely to be understood as exemplary data.

Figure 2A:
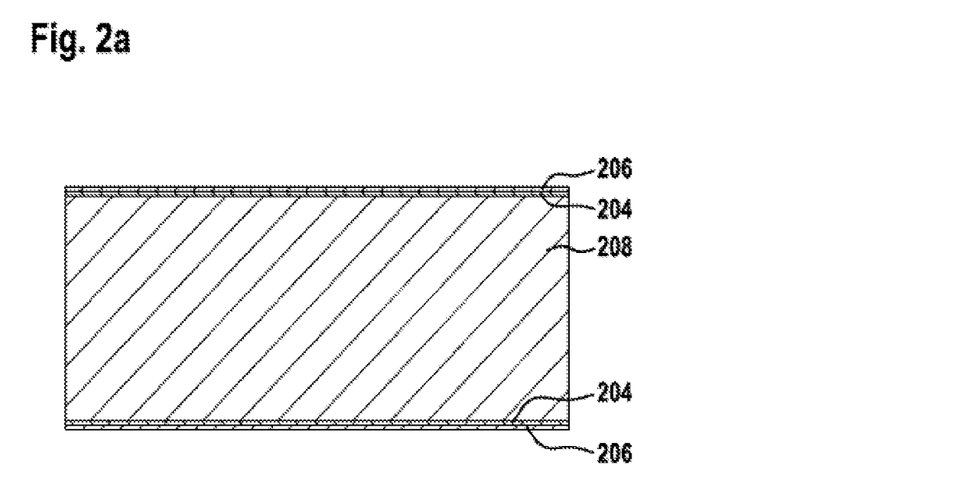
FIGS. 2a-2h show a schematic representation of a total process for producing a sequencing unit from FIG. 1.

FIGS. 2a to 2h show schematically a total process for producing a sequencing unit from FIG. 1. At the start of the process, a sequence of layers composed of, for example, 250 nm silicon dioxide 204 resulting from thermal oxidation and, thereabove, 280 nm silicon nitride 206 resulting from low-pressure vapor deposition is grown onto a front side and rear side of a silicon wafer 208 over the entire surface. This is shown in FIG. 2a. The compressive stress of the thermal silicon dioxide is compensated or overcompensated for by the tensile stress of the deposited silicon nitride. The specified layer thicknesses are only intended to illustrate how a tensile stress in the layer structure can be generated altogether through the interplay of compressively stressed and tensilely stressed layers through appropriate dimensioning of the layer thicknesses. The resulting tensile stress is important later in the process in order to avoid breaking of freed layer membranes by "arching" and to ensure sufficient stability.

Figure 2B:
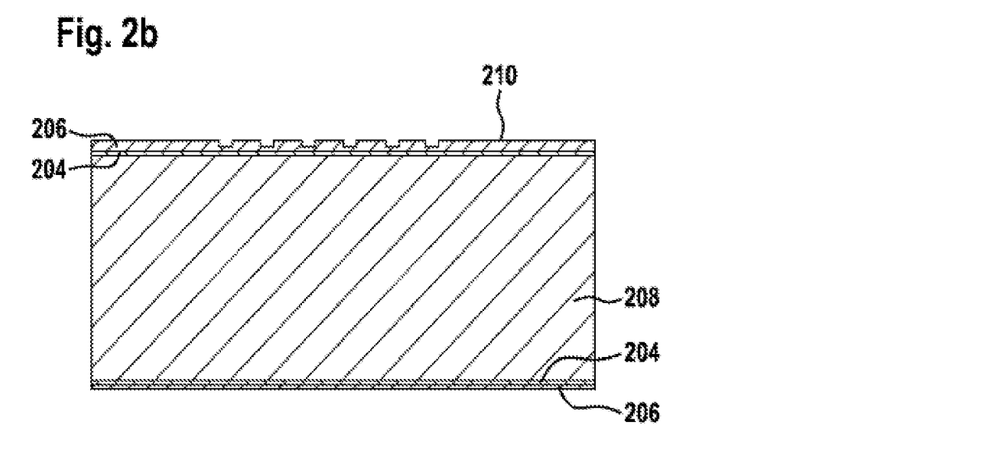
Figure 2C:
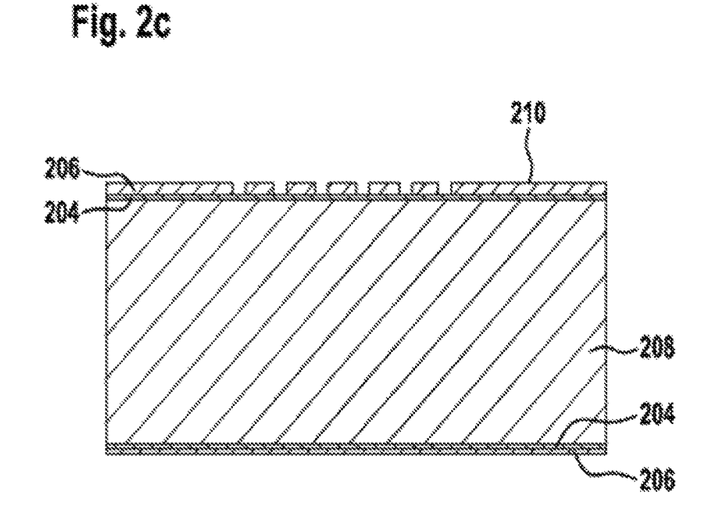
Figure 2D:
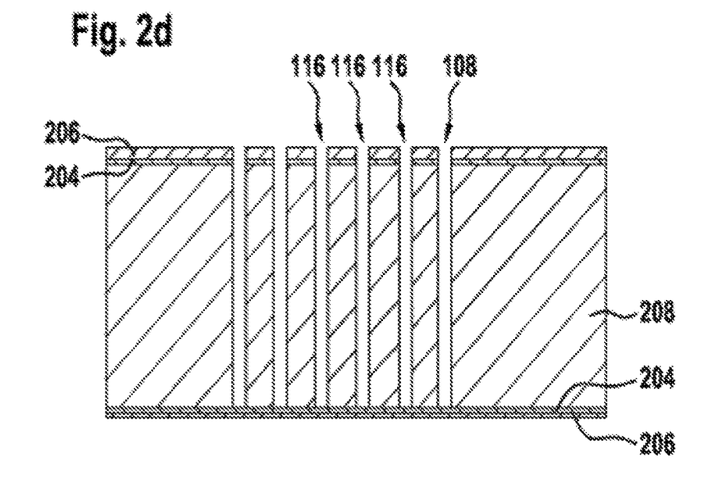

In a further process step, the geometries of qPCR array cell elements are defined on the front side of the wafer by photolithography using a sufficiently thick photoresist mask 210, as shown in FIG. 2b. In a self-adjusting process, the mask windows are first opened in the silicon nitride layer 206 and the silicon dioxide layer 204 by etching from the front side of the wafer. This is shown in FIG. 2c. Thereafter, using the same masking and by means of a DRIE process (DRIE=deep reactive ion etching), the caverns 108, 116 are etched through the silicon wafer 208 from the front side of the wafer as far as the stop on the silicon dioxide 204 of the rear side of the wafer. The result is shown in FIG. 2d. The caverns 108, 116 represent the later qPCR array cell elements. The thickness of the silicon dioxide layer 204 tolerates a certain overetching to compensate for deviations in etching-rate uniformity across the wafer surface. By way of example, it is assumed that, in the case of said overetching, up to 100 nm silicon dioxide can be lost in the cavern region. The silicon dioxide layer 204 thus has, in line with the exemplarily chosen initial layer thickness of 250 nm, additionally a residual thickness of 150 nm. The silicon dioxide layer 204 should not break through as far as the silicon nitride layer 206 during overetching, because silicon nitride does not have sufficient stability in the DRIE process. For a person skilled in the art, it is obvious what measures with respect to oxide thickness can allow an adjustment to a higher or lower overetching to be tolerated. After the silicon has been etched through, the membranes of the cavern bases are each self-supporting, i.e., should be tensilely stressed as mentioned above in order not to break and to have a sufficient stability for the follow-up processes.

Figure 2E:
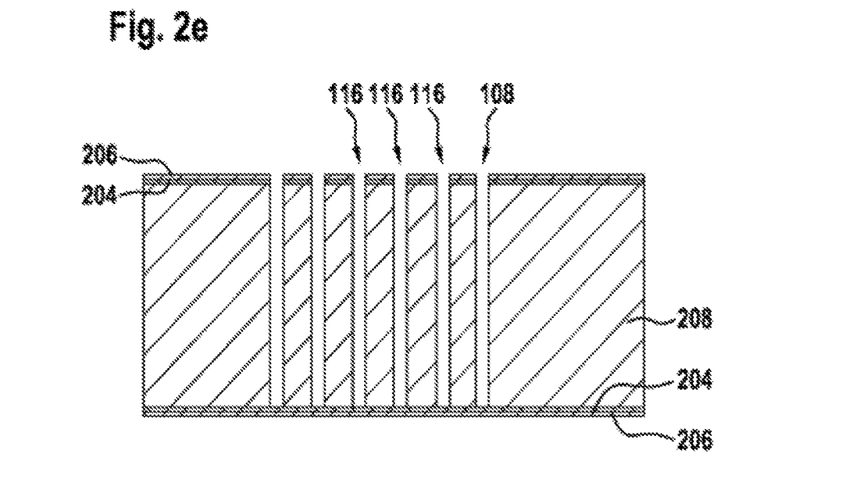
Figure 2F:
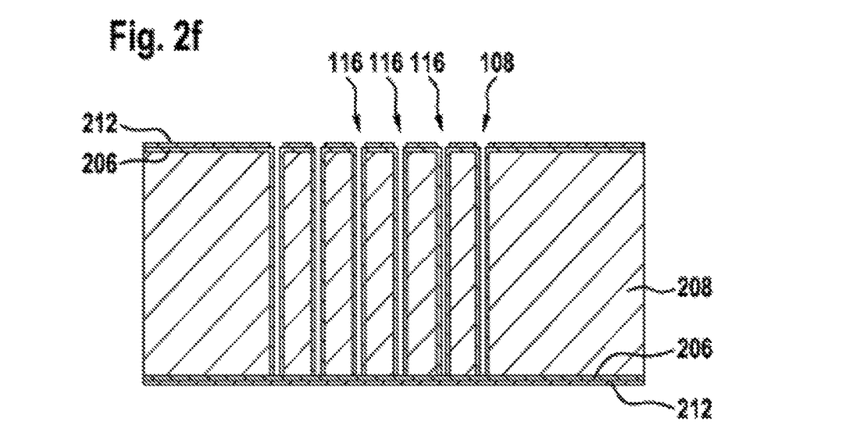

Thereafter, as shown in FIG. 2e, the photoresist mask 210 is removed from the front side of the wafer and the silicon wafer 208 is thermally oxidized, with, for example, 2.5 μm silicon dioxide being grown on the side walls of the caverns 108, 116 in the qPCR array cell elements. As a consequence of this thermal oxidation process, a portion of the silicon nitride layer 206 is likewise oxidized, but very much more slowly than is the case on free silicon surfaces. For 2.5 μm silicon dioxide grown thermally on silicon, what can be typically assumed is 30 nm silicon nitride which is converted into an approx. 40 nm thick Re oxide 212, i.e., silicon dioxide, as is evident from FIG. 2f.

Figure 2G:
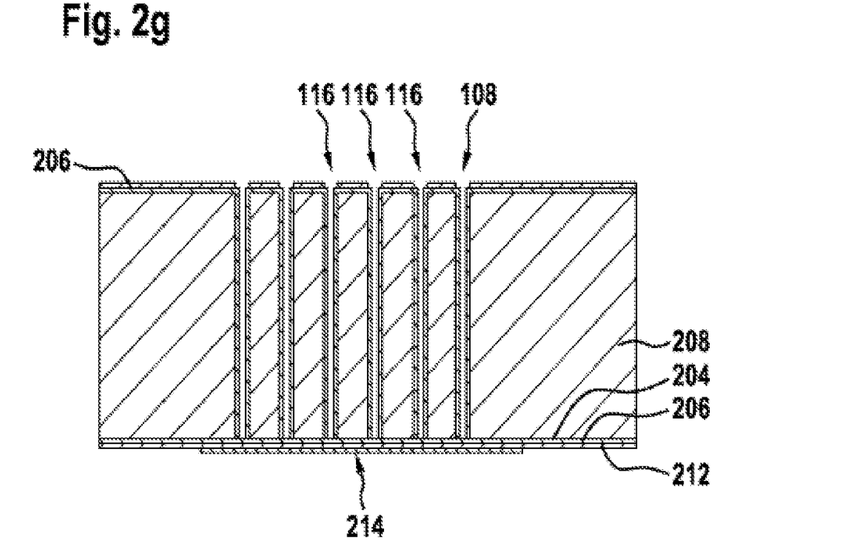

The Re oxide 212 has hydrophilic surface properties. If, on the front side in the follow-up process, it is removed from the front side of the wafer by selective etching, for example using buffered hydrofluoric acid, what arises is a comparatively hydrophobic front side of the wafer composed of silicon nitride, as shown in FIG. 2g. In the case of this etching process, approx. 50 to 100 nm silicon dioxide are likewise lost in the caverns 108, 116 on the side walls and on the cavern base, with the result that not less than 50 nm silicon dioxide 204 together with the overlying layer structure of approx. 250 nm silicon nitride and 40 nm Re oxide 212 remain on the cavern base, wherein the Re oxide 212 should not be removed from the rear side of the wafer. Since the rear side of the wafer remains hydrophilic owing to the Re oxide 212, what can then be carried out is the coating process to coat the rear side of the wafer with a precursor layer 214, in this case a self-assembled monolayer, for generating the graphene layer. After deposition, the monolayer 214 is provided with nanopores by means of t-SPL. Thereafter, a metallic layer is vapor-deposited onto the rear side of the wafer, for example 300 nm copper or nickel. The underlying monolayer 214 is thermally converted to graphene. At the same time, the annealing process also determines the size of the nanopores, since the carbon has a certain mobility during the temperature treatment and the 10 to 15 nm pores close up slowly from the edges proceeding from the t-SPL structuring of the monolayer 214.

Figure 2H:
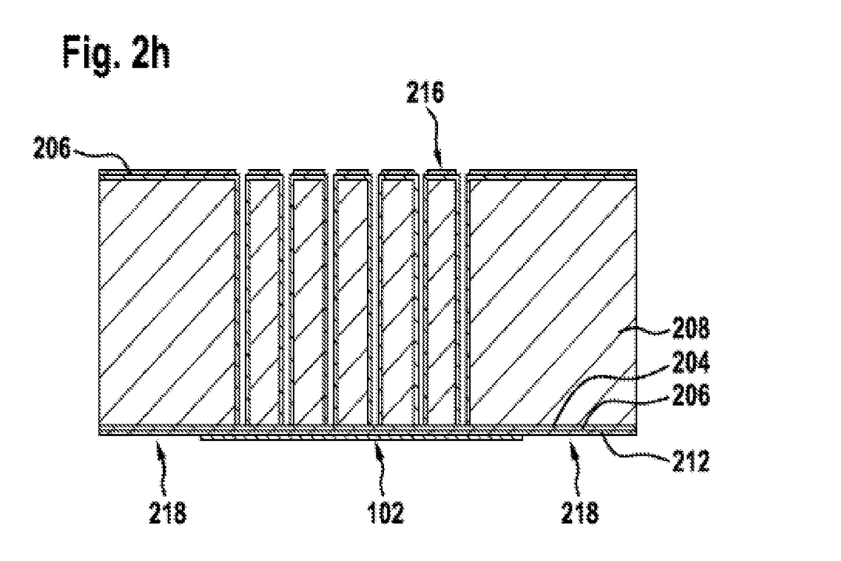

After removal of the metal layer, the graphene layer 102 with the generated nanopores is exposed on the layer structure of the cavern base. This is shown in FIG. 2h. Now, the layer structure of the cavern base is etched through in steps as far as the caverns 108, 114, specifically preferably by means of isotropically etching selective wet-etching chemistries, with the graphene layer 102 serving as masking for the etching process. Proceeding from the nanopores, the silicon dioxide layers are successively etched through from the rear side of the wafer, for example by means of highly dilute or buffered hydrofluoric acid, whereas phosphoric acid is used, for example, to etch through the silicon nitride interlayer. For the self-adjusting etching process with the aid of the nanopore-provided graphene layer 102 as masking, what are thus used in three steps are dilute (buffered) hydrofluoric acid for the Re oxide 212, phosphoric acid for the silicon nitride 206 and dilute (buffered) hydrofluoric acid for the underlying silicon dioxide 204. In the case of this procedure with use of the graphene nanopores as masking layer for the etching of the underlying dielectrics, a particular advantage achieved is that said dielectrics are substantially maintained outside the nanopores, mechanically support the graphene layer 102 and thus ensure additional stability.

After generation of a metallized layer 216 on the front side of the wafer and the bonding of a counter wafer to connection surfaces 218 on the rear side of the wafer, an array cell structure is available for connection to a measurement device, as schematically represented in FIG. 1.

A further advantage of this process sequence is that the front side of the wafer is relatively hydrophobic owing to the silicon nitride layer 206, whereas the cavern walls in the qPCR array cells are hydrophilic owing to the silicon dioxide layer 204 on the side walls and on the cavern base. This means that the qPCR array cells can be easily filled with aqueous media, since they are virtually sucked into the array cells and held therein owing to the hydrophilic environment. Furthermore, the closure of the array cells on the front side can be achieved particularly effectively, reliably and reproducibly by means of oils, preferably by means of fluorine oils or fluorocarbons of high dielectric strength and insulation such as perfluoropolyether or FC40 or FC77 (manufacturer: 3M), since the hydrophobic front side of the wafer repels a water film or a water film can be very easily and completely displaced therefrom by the advancing fluorine oils or fluorocarbons. As a result, both electrical and biochemical crosstalk between the array cell elements is suppressed in an effective manner, since a water film connecting the array cell elements is suppressed in an effective manner by the hydrophobic surface properties. The hydrophobic effect of the surface can, if needed, be additionally further enhanced, for example by printing with perfluoroalkyltrichlorosilanes such as, for example, perfluorooctyltrichlorosilane or perfluorodecyltrichlorosilane.

Figure 3:
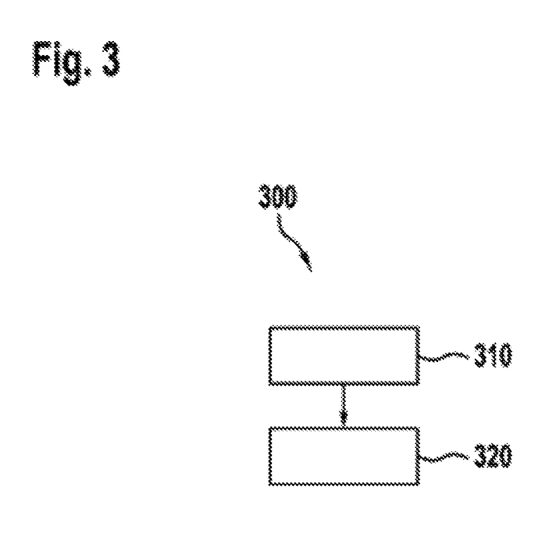
FIG. 3 shows a flow chart of a method according to one exemplary embodiment.

FIG. 3 shows a flow chart of a method 300 according to one exemplary embodiment. The method 300 can, for example, be carried out to produce a sequencing unit as described above on the basis of FIGS. 1 to 2h. This involves generating, in a step 310, a prestructured layer in a thermal lithography method by creating at least one sequencing pore in a precursor layer, especially a self-assembled monolayer. In a further step 320, it is converted into a graphene layer by heating to a particular conversion temperature. At the same time, the sequencing pore is reduced in size by a certain extent depending on the conversion temperature chosen.

By means of such a method, it is, for example, possible for nanopores of greater than 10 nm to be written into a self-assembled monolayer in a particularly economical manner by means of commercially available machines and commercially available processes and to be converted to a graphene layer having appropriate nanopores in a subsequent thermal process using a temporarily applied metal layer. Owing to carbon migration at high temperatures, the nanopores in the graphene can be reduced in size distinctly below the resolution limit of 10 to 15 nm of the thermal lithography process. Furthermore, a reduction of the layer thickness of the generated graphene layer immediately around the nanopores is advantageously achieved, typically from a bilayer or trilayer structure toward a monolayer structure, this increasing the accuracy of sequencing or the accuracy of determination of DNA fragment length. Since only comparatively few nanopores are written as points on the wafers, for example not more than two nanopores per qPCR array cell, the process of nanopore generation by means of t-SPL is extremely economical and rapidly performable.

If an exemplary embodiment comprises an "and/or" link between a first feature and a second feature, this is to be interpreted as meaning that the exemplary embodiment comprises both the first feature and the second feature according to one embodiment and either only the first feature or only the second feature according to a further embodiment.

The invention claimed is:

1. A method for producing a sequencing unit for sequencing a biochemical material, the method comprising:
   providing a graphene precursor layer;
   forming at least one pore in the graphene precursor layer using thermal lithography;
   thermally converting the graphene precursor layer with the at least one pore into a graphene layer by controlled heating of the graphene precursor layer to a selected conversion temperature using controlled annealing, thereby configuring the at least one pore as an at least one sequencing pore for sequencing the biochemical material;
   arranging a respective electrode at a respective opening of the at least one pore; and
   covering the graphene layer with a counter electrode.

2. The method as claimed in claim 1, wherein:
   a diameter of the formed at least one pore is reduced in size to a predetermined diameter by the thermal conversion.

3. The method as claimed in claim 1, wherein forming the at least one pore comprises:
   forming the at least one pore in the form of a nanopoint.

4. The method as claimed in claim 1, wherein forming the at least one pore comprises:
   forming the at least one pore with a diameter between 10 and 20 nanometers.

5. The method as claimed in claim 1, wherein thermally converting the graphene precursor layer with the at least one pore comprises:
   reducing the formed at least one pore to a diameter between 1 and 5 nanometers.

6. The method as claimed in claim 1, wherein thermally converting the graphene precursor layer with the at least one pore comprises:

converting the graphene precursor layer into a graphene monolayer at least in an edge region of the at least one pore.

7. The method as claimed in claim 1, wherein forming the at least one pore comprises:
   forming the at least one pore in a self-assembled monolayer as the graphene precursor layer.

8. The method as claimed in claim 1, further comprising:
   applying a metal layer to the graphene precursor layer with the at least one pore, wherein thermally converting the graphene precursor layer with the at least one pore comprises:
   applying heat to the graphene precursor layer with the at least one pore using the applied metal layer.

9. The method as claimed in claim 1, wherein forming the at least one pore further comprises:
   heating a pore segment of the graphene precursor layer to a temperature above a decomposition temperature of the graphene precursor layer thereby forming the at least one pore in the pore segment.

10. The method as claimed in claim 1, further comprising:
    forming, in a silicon wafer, at least one cavern having an entry opening and an exit opening configured to accommodate the biochemical material, wherein providing the graphene precursor layer comprises:
    applying the graphene precursor layer to a segment of the cavern element that has the exit opening prior to the forming the at least one pore, wherein forming the at least one pore comprises:
    forming the at least one pore in the graphene precursor layer opposite the exit opening.

11. The method as claimed in claim 10, wherein forming the at least one cavern comprises at least one of:
    forming an interior of the at least one cavern with a hydrophilic coating; and
    forming a segment of the cavern element that has the entry opening with a hydrophobic coating.

12. The method as claimed in claim 5, wherein thermally converting the graphene precursor layer comprises:
    reducing the formed at least one pore in size to a diameter between 1 and 2 nanometers.

13. The method of claim 1, further comprising:
    providing a silicon wafer;
    providing a front side silicon dioxide layer on the silicon wafer and a rear side silicon dioxide layer on the silicon wafer;
    providing a front side silicon nitride layer on the front side silicon dioxide layer and a rear side silicon nitride layer on the rear side silicon dioxide layer;
    defining a plurality of cell element geometries on a front side of the wafer with a photoresist mask formed on the front side silicon nitride layer;
    etching the front side of the wafer to open a plurality of mask windows through the front side silicon nitride layer;
    using a deep reactive ion etching process to etch a plurality of caverns through the front side silicon dioxide layer and at least partially through the silicon wafer through the opened plurality of mask windows;
    stopping the etching of the plurality of caverns using the rear side silicon dioxide layer;
    removing the photoresist mask; and
    growing silicon dioxide on sidewalls of the caverns, and forming a front side silicon dioxide layer and a rear side silicon dioxide layer using the front side silicon nitride layer and rear side silicon nitride layer, respectively, by thermal oxidation,
    wherein
    forming the at least one pore comprises forming a plurality of pores in the graphene precursor layer, each of the plurality of pores associated with a respective one of the plurality of caverns,
    the respective opening of each of the plurality of pores is an opening of the respective one of the plurality of caverns, and
    providing the graphene precursor layer comprises coating the rear side silicon dioxide layer with the graphene precursor layer.

14. The method of claim 13, further comprising:
    vapor-depositing a metallic layer onto the graphene precursor layer after forming the at least one pore, wherein the metallic layer is used in the thermally converting the graphene precursor layer into the graphene layer;
    removing a residual of the metallic layer after thermally converting the graphene precursor layer into the graphene layer; and
    using the at least one pore configured as an at least one sequencing pore as a mask to isotropically etch the rear side silicon dioxide layer and the rear side silicon nitride layer.

15. The method of claim 14, further comprising:
    etching the front side silicon dioxide layer prior to coating the rear side silicon dioxide layer with the graphene precursor layer.

16. The method of claim 13, wherein when forming the at least one pore in the graphene precursor layer using thermal lithography a thermal scanning probe is used to form each of the at least one pore at a location spaced apart from any of the other at least one pore.

* * * * *